United States Patent
Le Roux et al.

(10) Patent No.: US 10,265,105 B2
(45) Date of Patent: Apr. 23, 2019

(54) SURGICAL ASSEMBLY, AND BONE ANCHOR SCREW AND DEVICE FOR EXTENDING ONE SUCH SCREW THAT BELONG TO SAID SURGICAL ASSEMBLY

(71) Applicant: SPINEWAY, Ecully (FR)

(72) Inventors: Stephane Le Roux, Lyons (FR); Philippe Laurito, Le Val (FR); Julien Bazille, Lyons (FR)

(73) Assignee: SPINEWAY, Ecully (FR)

( * ) Notice: Subject to any disclaimer, the term of this patent is extended or adjusted under 35 U.S.C. 154(b) by 21 days.

(21) Appl. No.: 15/127,595

(22) PCT Filed: Mar. 4, 2015

(86) PCT No.: PCT/FR2015/050535
§ 371 (c)(1),
(2) Date: Sep. 20, 2016

(87) PCT Pub. No.: WO2015/140440
PCT Pub. Date: Sep. 24, 2015

(65) Prior Publication Data
US 2017/0164980 A1    Jun. 15, 2017

(30) Foreign Application Priority Data
Mar. 20, 2014 (FR) ...................... 14 52299

(51) Int. Cl.
*A61B 17/70* (2006.01)
(52) U.S. Cl.
CPC ........ *A61B 17/708* (2013.01); *A61B 17/7032* (2013.01); *A61B 17/7076* (2013.01)
(58) Field of Classification Search
CPC .......................... A61B 17/708; A61B 17/7032
See application file for complete search history.

(56) References Cited

U.S. PATENT DOCUMENTS 9,198,698 B1 * 12/2015 Doose ................... A61B 17/708
9,333,012 B2 * 5/2016 Beale ................. A61B 17/7076
(Continued)

FOREIGN PATENT DOCUMENTS

EP       2692304 A1     2/2014

OTHER PUBLICATIONS

International Search Report and Written Opinion issued in PCT/FR2015/050535, dated May 15, 2015.

*Primary Examiner* — Jan Christopher L Merene
(74) *Attorney, Agent, or Firm* — Heslin Rothenberg Farley & Mesiti P.C.

(57) ABSTRACT

The surgical assembly includes: a bone anchorage screw having an anchorage portion for anchoring in a vertebral column, and a head in the form of a socket; and an extension device adapted to fit over the socket of the bone anchorage screw for forming a longitudinal extension thereto. The extension device includes a first tubular element referred to as an "inner tube", of inside diameter greater than or equal to the inside diameter of the socket of the bone anchorage screw, and extended longitudinally by two diametrically opposite branches, forming jaws for clamping onto the outside surface of the socket so as to lock onto the socket, and a second tubular element referred to as an "outer tube", mounted to slide along said inner tube. The outer tube is extended longitudinally by two diametrically opposite branches having their free ends in register with the free ends of the two branches of the inner tube, and being provided with retaining means for co-operating with complementary retaining means arranged on the socket to prevent the branches from moving apart from each.

10 Claims, 8 Drawing Sheets

(56) References Cited

U.S. PATENT DOCUMENTS

| | | | | |
|---|---|---|---|---|
| 9,433,446 B2* | 9/2016 | McLean | | A61B 17/7032 |
| 9,492,209 B2* | 11/2016 | Biedermann | | A61B 17/7085 |
| 9,526,553 B2* | 12/2016 | Bess | | A61B 17/7082 |
| 9,572,604 B2* | 2/2017 | Petit | | A61B 17/7032 |
| 9,668,789 B2* | 6/2017 | Barrett | | A61B 17/708 |
| 2005/0131408 A1* | 6/2005 | Sicvol | | A61B 17/7032 |
| | | | | 606/86 A |
| 2007/0233155 A1* | 10/2007 | Lovell | | A61B 17/7076 |
| | | | | 606/104 |
| 2008/0082103 A1* | 4/2008 | Hutton | | A61B 17/0218 |
| | | | | 606/272 |
| 2008/0125817 A1* | 5/2008 | Arnett | | A61B 17/7002 |
| | | | | 606/319 |
| 2008/0312693 A1* | 12/2008 | Trautwein | | A61B 17/1757 |
| | | | | 606/246 |
| 2010/0137875 A1* | 6/2010 | Marino | | A61B 17/7002 |
| | | | | 606/104 |
| 2012/0022594 A1* | 1/2012 | Walker | | A61B 17/708 |
| | | | | 606/264 |
| 2012/0203279 A1* | 8/2012 | Walters | | A61B 17/7077 |
| | | | | 606/252 |
| 2013/0096635 A1* | 4/2013 | Wall | | A61B 17/7085 |
| | | | | 606/305 |
| 2013/0103094 A1* | 4/2013 | Beale | | A61B 17/7076 |
| | | | | 606/279 |
| 2013/0245702 A1* | 9/2013 | McBride | | A61B 17/7076 |
| | | | | 606/305 |
| 2014/0046372 A1* | 2/2014 | Ibrahim | | A61B 17/7034 |
| | | | | 606/250 |
| 2014/0052187 A1* | 2/2014 | McBride | | A61B 17/708 |
| | | | | 606/264 |
| 2014/0052817 A1* | 2/2014 | Long | | H04L 67/2857 |
| | | | | 709/217 |
| 2015/0112397 A1* | 4/2015 | Petit | | A61B 17/7076 |
| | | | | 606/86 A |
| 2015/0164495 A1* | 6/2015 | Petit | | A61B 17/708 |
| | | | | 600/210 |
| 2015/0164569 A1* | 6/2015 | Reitblat | | A61B 17/7077 |
| | | | | 606/279 |
| 2015/0359571 A1* | 12/2015 | Biedermann | | A61B 17/7076 |
| | | | | 606/246 |
| 2016/0106480 A1* | 4/2016 | Zhou | | A61B 17/7002 |
| | | | | 606/86 A |
| 2017/0027612 A1* | 2/2017 | Viart | | A61B 17/708 |
| 2017/0042524 A1* | 2/2017 | Angus | | A61B 17/025 |
| 2017/0049428 A1* | 2/2017 | Cryder | | A61B 17/025 |
| 2017/0079696 A1* | 3/2017 | Walker | | A61B 17/708 |
| 2017/0095272 A1* | 4/2017 | Hutton | | A61B 17/708 |
| 2017/0100116 A1* | 4/2017 | Erramilli | | A61B 17/7035 |
| 2017/0100164 A1* | 4/2017 | Landry | | A61B 17/708 |
| 2017/0112539 A1* | 4/2017 | Hayes | | A61B 17/708 |
| 2017/0143323 A1* | 5/2017 | Cryder | | A61B 17/025 |
| 2017/0156761 A1* | 6/2017 | Sicvol | | A61B 17/708 |
| 2017/0156762 A1* | 6/2017 | Sicvol | | A61B 17/708 |
| 2017/0164980 A1* | 6/2017 | Le Roux | | A61B 17/708 |
| 2017/0164985 A1* | 6/2017 | Reitblat | | A61B 17/7085 |
| 2017/0172627 A1* | 6/2017 | Kruger | | A61B 17/7032 |
| 2017/0189083 A1* | 7/2017 | Barrett | | A61B 17/7086 |
| 2017/0196601 A1* | 7/2017 | Koenig | | A61B 17/7092 |
| 2017/0209179 A1* | 7/2017 | Ferreira | | A61B 17/708 |
| 2017/0224392 A1* | 8/2017 | Choi | | A61B 17/7079 |
| 2017/0252072 A1* | 9/2017 | Artaki | | A61B 17/7074 |
| 2017/0252120 A1* | 9/2017 | Fallin | | A61B 17/7085 |
| 2017/0265850 A1* | 9/2017 | Cryder | | A61B 17/025 |
| 2017/0311995 A1* | 11/2017 | Wall | | A61B 17/7076 |
| 2017/0319245 A1* | 11/2017 | Gephart | | A61B 17/7043 |
| 2017/0360486 A1* | 12/2017 | Semingson | | A61B 17/7082 |
| 2018/0000521 A1* | 1/2018 | Arnold | | A61B 17/8875 |
| 2018/0008318 A1* | 1/2018 | Fiechter | | A61B 17/708 |
| 2018/0008324 A1* | 1/2018 | Cryder | | A61B 17/7086 |

* cited by examiner

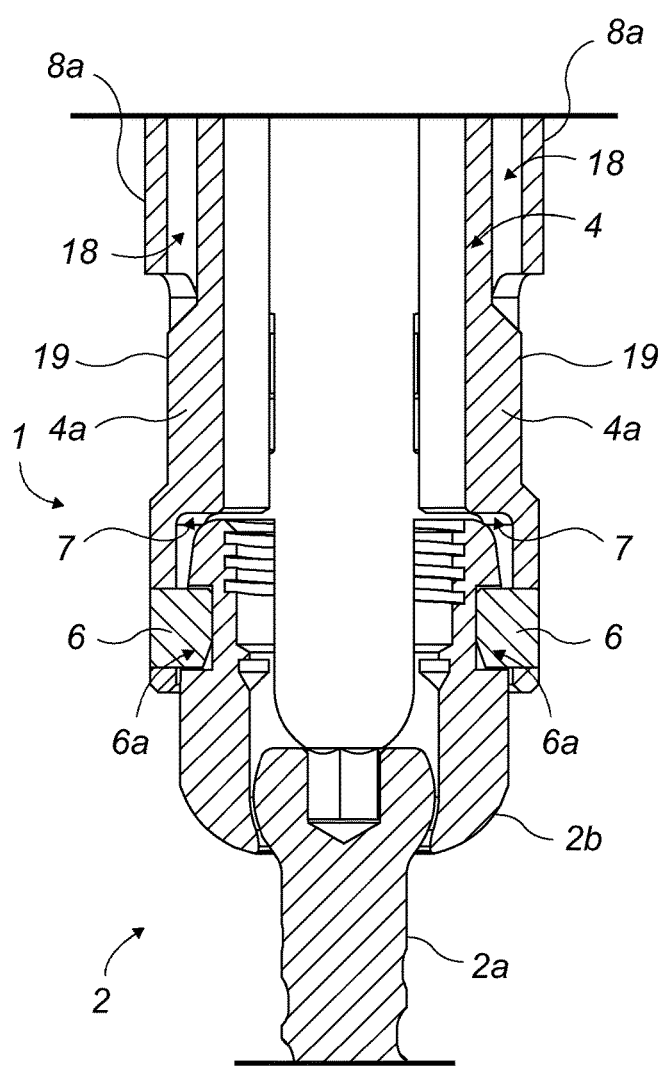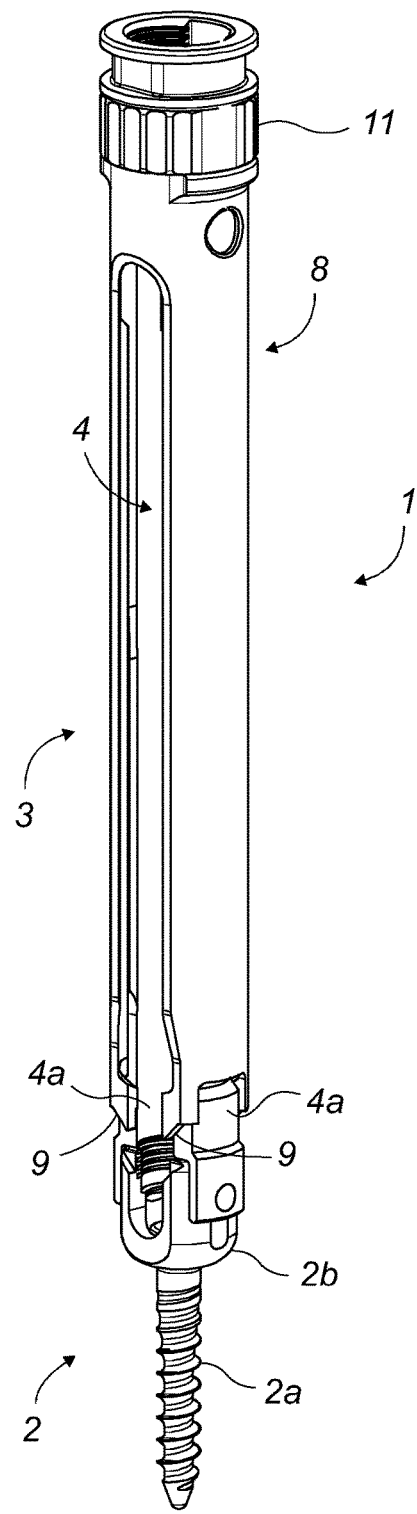
FIG.7
FIG.8

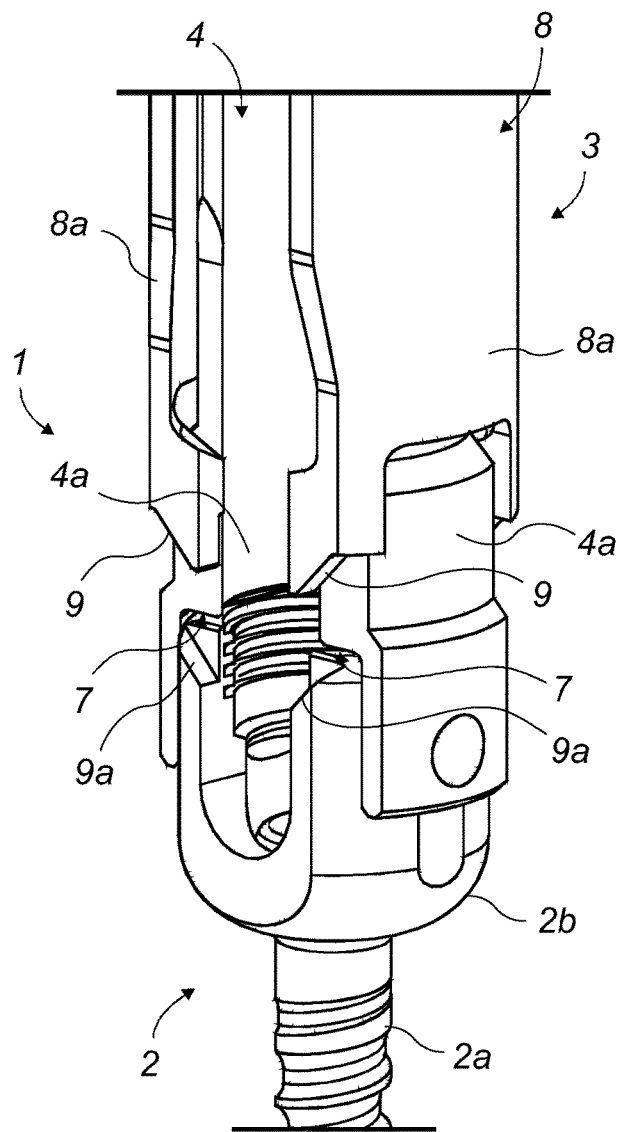
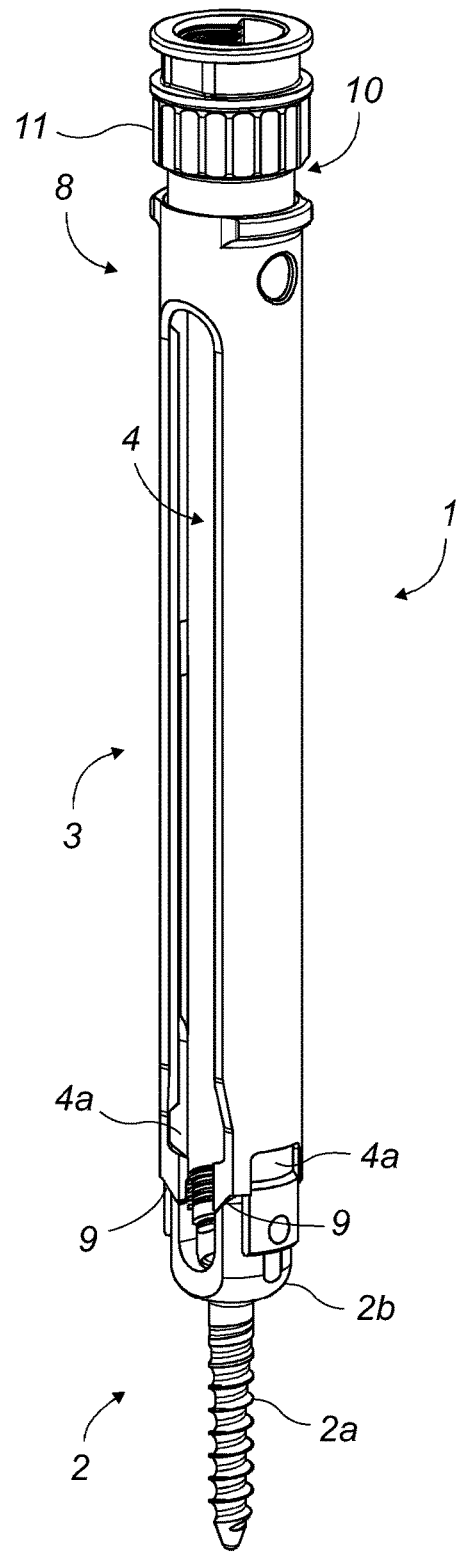
FIG.9
FIG.10

SURGICAL ASSEMBLY, AND BONE ANCHOR SCREW AND DEVICE FOR EXTENDING ONE SUCH SCREW THAT BELONG TO SAID SURGICAL ASSEMBLY

CROSS REFERENCE TO RELATED APPLICATIONS

This application is a national stage filing under section 371 of International Application No. PCT/FR2015/050535, filed on Mar. 4, 2015, and published in English on Sep. 24, 2015, as WO 2015/140440 A1 and claims priority of French application no. 1452299 filed on Mar. 20, 2014, the entire disclosure of these applications being hereby incorporated herein by reference.

TECHNICAL FIELD

The present invention relates to the technical sector of surgical instruments.

The invention may be advantageously applied to treating chronic instabilities, fractures or deformations of the spine, and in particular it may be applied to a minimally invasive posterior approach.

However, the invention may be transposed to all applications in which a bone anchorage screw is implanted by a surgeon.

STATE OF THE PRIOR ART

In the field of spinal osteosynthesis, it is very well known for spinal implants to be used that implement at least two bone anchorage screws, in particular pedicle screws, designed to be screwed into the vertebra, and a link system (plate or rod) uniting the two pedicle screws so as to achieve distraction or compression, and so as to redefine the curvature of the vertebral column. The head of a bone anchorage screw is generally in the form of a socket suitable for transversely receiving said link tube, and for longitudinally receiving a locking member for locking the link tube in the head of the screw.

In the context of implantation by a minimally invasive approach, such pedicle screws are difficult for the surgeon to implant and to manipulate because the access is relatively narrow. It is common practice to use extension devices for extending pedicle screws in order to help the surgeon, firstly to implant and to manipulate the pedicle screws, and, secondly to put in place the link rods of said pedicle screws.

The extension device and the pedicle screw may be adapted to fit together to form a surgical assembly for treating instabilities, fractures or deformations of a vertebral column.

A known extension device is in the form of a tubular element having one of its ends suitable for being fastened temporarily to the head of the pedicle screw. The tubular element is such that it allows free access to the screw head, and such that it allows a locking member to be inserted for locking a link rod, and a tool to be inserted for locking said locking member.

For this purpose, the end of the tubular element may be in the form of jaws suitable for clamping around the outside wall of the pedicle screw head.

On their inside surfaces facing the screw head, the jaws may have arrangements suitable for co-operating with complementary arrangements provided on the screw head for the purpose of temporarily locking the co-operation between said screw head and the extension device.

However, such arrangements are often not sufficient to hold the screw head optimally in engagement with the end of the extension device.

SUMMARY OF THE INVENTION

An object of the invention is thus to remedy at least the above-mentioned drawbacks by proposing a surgical assembly comprising a bone anchorage screw and an extension device that make it possible to preserve access to the socket of the bone anchorage screw during the surgical operation, while also optimally holding said extension device temporarily on said screw head.

Another object of the invention is to provide an extension device that makes it possible facilitate putting in place bone anchorage screw link rods, and to facilitate putting in place locking members for locking said link rods in the sockets of the bone anchorage screws.

To this end, the invention provides a surgical assembly, for example for treating instabilities, fractures or deformations of the vertebral column, said assembly comprising:
  a bone anchorage screw having an anchorage portion for anchoring in the vertebral column, and a head in the form of a socket; and
  an extension device designed to come to fit over the socket of the bone anchorage screw for forming a longitudinal extension thereto.

In accordance with the invention, the extension device comprises a first tubular element referred to as an "inner tube", of inside diameter greater than or equal to the inside diameter of the socket of the bone anchorage screw to be fitted over. The inner tube is extended longitudinally by two diametrically opposite branches. Said branches have resilience allowing them to be moved apart from each other and towards each other. The free ends of the two branches form jaws suitable for clamping onto the outside surface of the socket so as to lock onto it.

Also in accordance with the invention, the extension device further comprises a second tubular element referred to as an "outer tube", mounted around the inner tube, and of inside diameter matching the outside diameter of said inner tube to an extent such that said outer tube can slide along said inner tube between a "non-locking position" and a "locking position", in which positions it respectively does not lock onto and locks onto the bone anchorage screw. The outer tube is extended longitudinally by two diametrically opposite branches that are superposed on the branches of the inner tube. The free ends of the two branches of the outer tube are in register with the free ends of the two branches of the inner tube, and each of said free ends of the outer tube is provided with retaining means suitable, when the extension device is fitted over the socket of the bone anchorage screw and when said outer tube is slid into its locking position, for co-operating with complementary retaining means arranged on the socket to prevent said branches of the outer tube from moving apart from each other, thereby preventing the branches of the inner tube from moving apart from each other so as to make it possible to keep the extension device locked on the socket of the bone anchorage screw.

In this way, the extension device can fit over the socket of a bone anchorage screw in such a manner as to form a longitudinal extension thereto for facilitating manipulation and implanting of the bone anchorage screw. The inside diameter of the inner tube is greater than or equal to the inside diameter of the socket, so that the extension device makes it possible to preserve access to the socket of the bone anchorage screw via the inside of said inner tube. Locking of the extension onto the socket is optimum. The inner and outer tubes are extended by diametrically opposite branches so as to provide space between said branches for allowing a transverse link rod to be put in place that can be put in place by being slid to the socket of the bone anchorage screw.

In a particular embodiment, the complementary retaining means are contact surfaces provided at the ends of the branches of the outer tube and on the socket. Said contact surfaces are designed to come to bear against one another when the device fits over a bone anchorage screw, and when the outer tube is slid into its locking position for preventing the branches of the outer tube from moving apart from each other.

Advantageously, complementary fastening means suitable for locking said branches of the inner tube so that they are prevented from moving longitudinally relative to the outside surface of the socket are arranged firstly at the free ends of the branches of the inner tube and on the inside surfaces of said branches that are designed to be in contact with the outside surface of the socket, and secondly on said outside surface of the socket.

In this way, the locking of the extension device onto the socket is even more effective. The complementary fastening means are suitable for locking the branches of the inner tube so as to prevent them from moving longitudinally, so that it is then necessary to move said branches apart from each other in order to unlock the device. And, in the locking position, the outer tube prevents said branches of the inner tube from moving apart from each other. The locking is optimum.

In a particular embodiment, the complementary fastening means are of the type consisting of mutually complementary lugs and recesses that are suitable for co-operating with one another.

The invention also and separately provides an extension device and a bone anchorage screw that have the above-mentioned characteristics and that are part of a surgical assembly as mentioned above.

Advantageously, in the extension device of the invention, at least one of the branches of the inner tube has, at its free end, a transverse shoulder suitable for forming an abutment against a socket of a bone anchorage screw when said extension device comes to fit over said socket.

In accordance with another characteristic, the extension device is provided with a locking member suitable for holding the outer tube in the locking position in which it locks onto the bone anchorage screw.

Advantageously, the inner tube and the outer tube are also provided with complementary guide means suitable for preventing said outer tube from turning relative to said inner tube.

In addition, on its inside surface, each of the branches of the inner tube has a projection or shoulder. Said projections are diametrically opposite each other and in register with each other so that, when an appropriate tool is inserted into the inner tube, said tool comes into abutment against said projections so as to force the branches of the inner tube to move apart from each other.

Preferably, the extension device of the invention further comprises a tool in the form of a rod suitable for being inserted into the inner tube of said extension device so as to come into abutment against the projections or shoulders and so as to force the branches of the inner tube to move apart from each other.

BRIEF DESCRIPTION OF THE DRAWINGS

Other characteristics and advantages of the invention appear clearly from the following description that is given by way of non-limiting indication, with reference to the accompanying figures, in which:

FIG. 7 is a diagrammatic view similar to the FIG. 6 view, the surgical assembly being shown in longitudinal section and from the front;

FIG. 8 is a diagrammatic perspective view showing the surgical assembly of the invention, with the extension device fitting over the socket of a pedicle screw;

FIG. 9 is a diagrammatic perspective view similar to the FIG. 8 view, showing in detail the co-operation between the extension device and the pedicle screw;

FIG. 10 is a diagrammatic perspective view similar to the FIG. 8 view, with the outer tube of the extension device being slid into its locking position in which it locks onto the pedicle screw;

DETAILED DESCRIPTION OF THE INVENTION

The invention relates to a surgical assembly (1). By way of example, a description follows of a surgical assembly (1) for treating instabilities, fractures or deformations of the vertebral column. However, naturally said surgical assembly may be transposed to all applications in which a bone anchorage screw is implanted by a surgeon. In the application described in detail below, the bone anchorage screw is a pedicle screw.

Figures 1, 2:
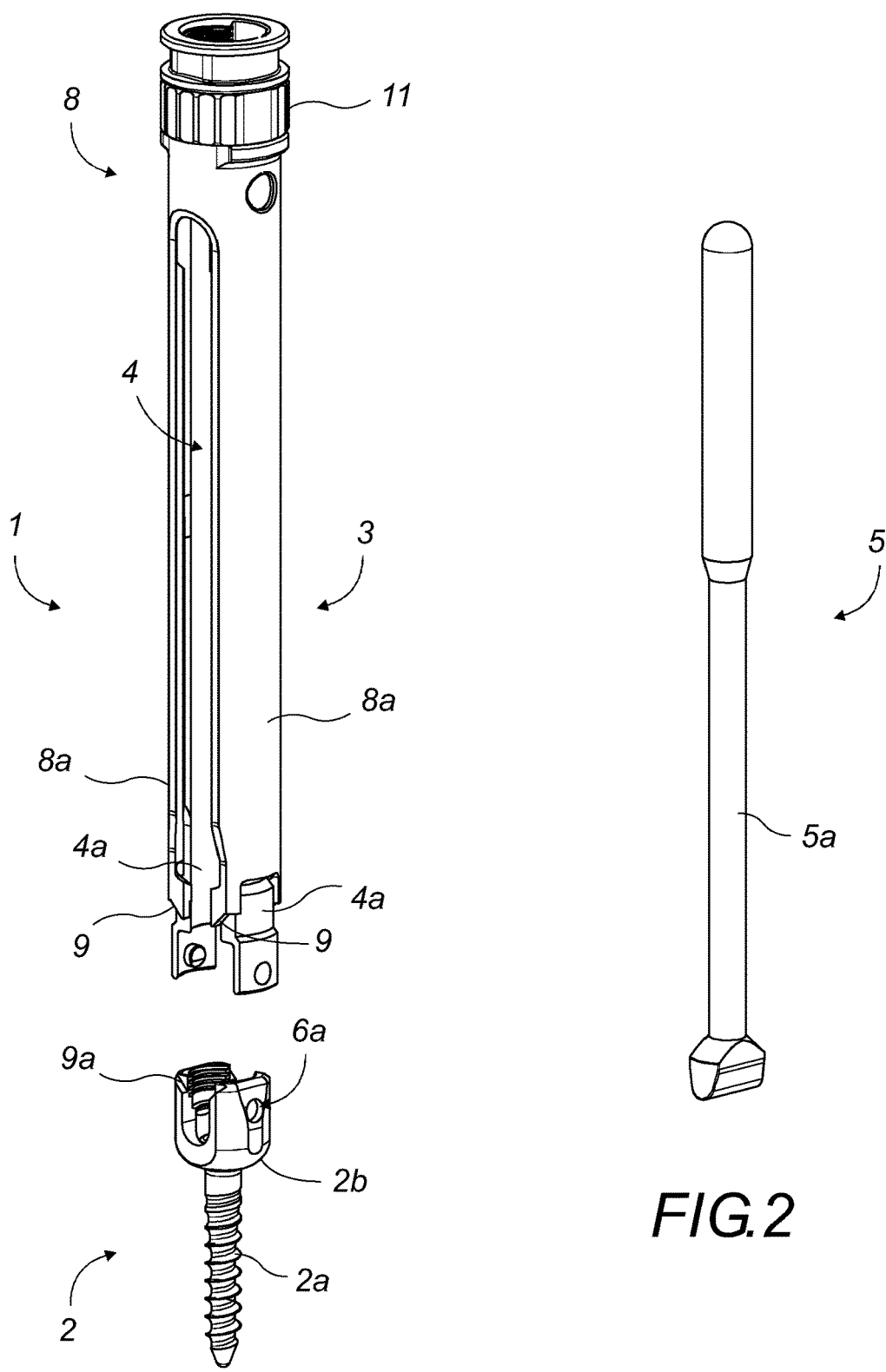
FIG. 1 is a diagrammatic perspective view of a surgical assembly of the invention for treating instabilities, fractures or deformations of a vertebral column, before the extension device comes to fit over the bone anchorage screw, and in particular the pedicle screw.
FIG. 2 is a diagrammatic perspective view of a tool for assisting with putting in place the extension device of the invention.

With reference to FIG. 1, the assembly (1) comprises, separately, a pedicle screw (2) and an extension device (3) for extending the pedicle screw (2), the screw and the extension device being adapted to co-operate temporarily with each other for the time it takes to perform a surgical operation for treating instabilities, fractures or deformations of the vertebral column.

The pedicle screw (2) comprises an anchorage portion (2a) for anchoring in the vertebral column, and a head in the form of a socket (2b). The socket (2b) is suitable for transversely receiving a link rod (not shown) and a locking member (not shown) for locking the link rod that are part of a spinal implant that is well known to the person skilled in the art. The socket (2b) of the pedicle screw (2) is suitable for receiving the extension device (3) of the invention.

The extension device (3) includes a first tubular element referred to as the "inner tube" (4). In order to provide unobstructed access to the socket (2b) from the inside of said inner tube (4), the inner tube (4) has an inside diameter greater than or equal to the inside diameter of the socket (2b) over which the extension device is to fit. The inner tube (4) then permits insertion of a tool (not shown) for manipulating the head of the pedicle screw (2), a tool (5) for assisting with putting the extension device (3) into place over the socket (2b) or for assisting with removing it therefrom, or indeed the inner tube (4) then permits insertion of a locking member (not shown) designed to co-operate with the screw head for locking a link rod for linking two pedicle screws (2) together.

Figures 3, 4:
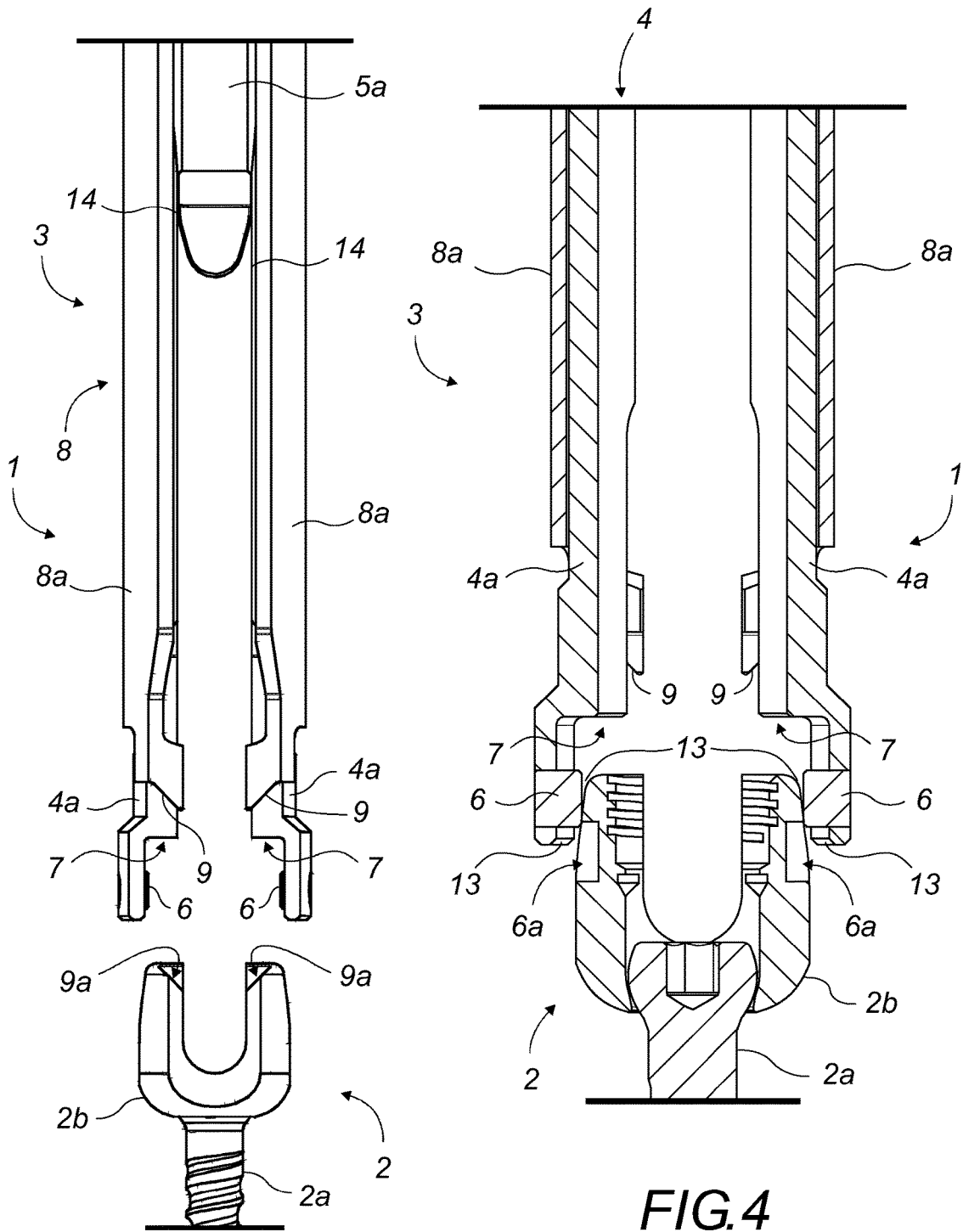
FIG. 3 is a diagrammatic front view showing in detail the end of the extension device before it comes to fit over the socket of a pedicle screw, with the tool for assisting with putting in place being present.
FIG. 4 is a diagrammatic view similar to the diagrammatic view of FIG. 3, showing in longitudinal section and from the front how the extension device is put in place over the socket of a pedicle screw.

With reference to FIGS. 3 and 4, the inner tube (4) is extended longitudinally by two diametrically opposite branches (4a). The branches (4a) have resilience enabling them to be moved apart from each other or moved towards each other, and the free ends of the two branches (4a) form jaws designed to clamp onto the outside surface of the socket (2b) so as to lock onto it. The resilience of the branches (4a) makes it possible, in part, to keep the extension device (3) locked onto the socket (2b).

In advantageous manner, each of the free ends of the branches (4a) of the inner tube (4) is provided with a lug (6) arranged on its inside surface and designed to be in contact with the outside surface of the socket (2b). In corresponding manner, the outside surface of the socket (2b) of the pedicle screw (2) of the invention is provided with two diametrically opposite recesses (6a) that are suitable for engagably receiving the lugs (6) on the free ends of the branches (4a) of the inner tube (4).

With reference to FIG. 7, when the lugs (6) co-operate with the complementary recesses (6a) in the socket (2b), they are suitable for locking said branches (4a) of the inner tube (4) so as to prevent them from moving longitudinally relative to the outside surface of the socket (2b). In other words, when the branches (4a) of the inner tube (4) are locked onto the socket (2b), it then becomes necessary to move the branches (4a) apart from each other in order to release the lugs (6) from the recesses (6a) and in order to unlock the extension device (3).

The branches (4a) of the inner tube (4) thus come to fit over the socket (2b) (see FIGS. 8 and 9), and each of said branches has, at its free end, a transverse shoulder (7) suitable for forming an abutment against the socket (2b) of a pedicle screw (2) when said extension device (3) comes to fit over said socket (2b). The co-operation between the socket (2b) and the extension device (3) is then controlled.

The extension device (3) further includes a second tubular element referred to as an "outer tube" (8) and mounted around the inner tube (4). The inside diameter of the outer tube (8) matches the outside diameter of said inner tube (4) to such an extent that the outer tube can slide along said inner tube (4) between a non-locking position and a locking position, in which positions it respectively does not lock onto and locks onto a pedicle screw (2) (see FIGS. 10, 11, 12).

The outer tube (8) is extended longitudinally by two diametrically opposite branches (8a) that are superposed on the branches (4a) of the inner tube (4). The branches (4a) of the inner tube (4), and the branches (8a) of the outer tube (8) are diametrically opposite and are spaced apart from each other in such a manner as to allow a transverse link rod (not shown) to be inserted between the branches (4a, 8a) of each tube (4, 8). Said link tube can then be slid in known manner to the socket (2b) of the pedicle screw (2) when the extension device (3) fits over said socket (2b).

The branches (8a) of the outer tube (8) also have resilience allowing them to be moved apart from each other or towards each other so as not to prevent the branches (4a) of the inner tube (4) from being moved apart from each other when the outer tube (8) is in its non-locking position.

However, it is not essential for the branches (8a) of the outer tube (8) to have resilience. With reference to FIG. 7, clearance (18) remains between the inner tube (4) and the outer tube (8). This clearance (18) enables the branches (4a) of the inner tube (4) to move apart from each other. A shoulder (19) provided on the outside surface of the inner tube (4) makes it possible to take up the clearance (18) after locking, i.e. after the outer tube (8) has slid around the inner tube (4) towards the pedicle screw (2). Before locking, the outer tube (8) lies above said shoulder (19), and after locking, it lies at the same level as said shoulder (19).

The free ends of the two branches (8a) of the outer tube (8), like the free ends of the inner tube (4), are designed to come into register with the pedicle screw (2) when the extension device (3) comes to fit over the socket (2b) of a pedicle screw (2). Each of said free ends of the branches (8a) of the outer tube (8) has contact surfaces (9) suitable, when said outer tube (8) is slid into its locking position, for coming to bear against complementary contact surfaces (9a) provided on the socket (2b) of the pedicle screw (2) that is part of the surgical assembly (1), and over which said extension device (3) is fitted.

The contact surfaces (9) of each of the branches (8a) of the outer tube (8) are inclined relative to the transverse plane of the outer tube (8), and face outwards from each branch (8a), in register with the direction in which said branch (8a) moves apart from the other one. The contact surfaces (9) of one of the branches (8a) are diametrically opposite, symmetrical, and in register with the contact surfaces (9) of the other branch (8a).

The contact surfaces (9a) of the socket (2b) correspond to the contact surfaces (9) of the branches (8a) of the outer tube (8), and are inclined relative to the transverse plane of said socket (2b). Said contact surfaces (9a) of the socket (2b) are diametrically opposite, and face towards the inside of the socket (2b). The term "contact surfaces" (9, 9a) is used to mean, in particular, inclined faces.

The co-operation between said contact surfaces (9, 9a) is such that it opposes moving apart of the branches (8a) of the outer tube (8). The branches (8a) of the outer tube (8) are superposed on the branches (4a) of the inner tube (4), and the inside diameter of the outer tube (8) matches the outside diameter of the inner tube (4), so that, if the branches (8a)

of the outer tube (8) cannot move apart from each other, said branches (8a) also prevent the branches (4a) of the inner tube (4) from moving apart from each other. Thus, when the branches (4a) of the inner tube (4) are locked onto the outside surface of the socket (2b) of the pedicle screw (2), and when the outer tube (8) is slid into the locking position, the branches (8a) of the outer tube (8) prevent the branches (4a) of the inner tube (4) from moving apart from each other and thus from unlocking. The extension device (3) is then held optimally in its locking position.

For holding the outer tube (8) in its locking position, and thus for keeping the extension device (3) locked onto the socket (2b) of the pedicle screw (2), the extension device (3) is provided with a locking member.

Figure 13:
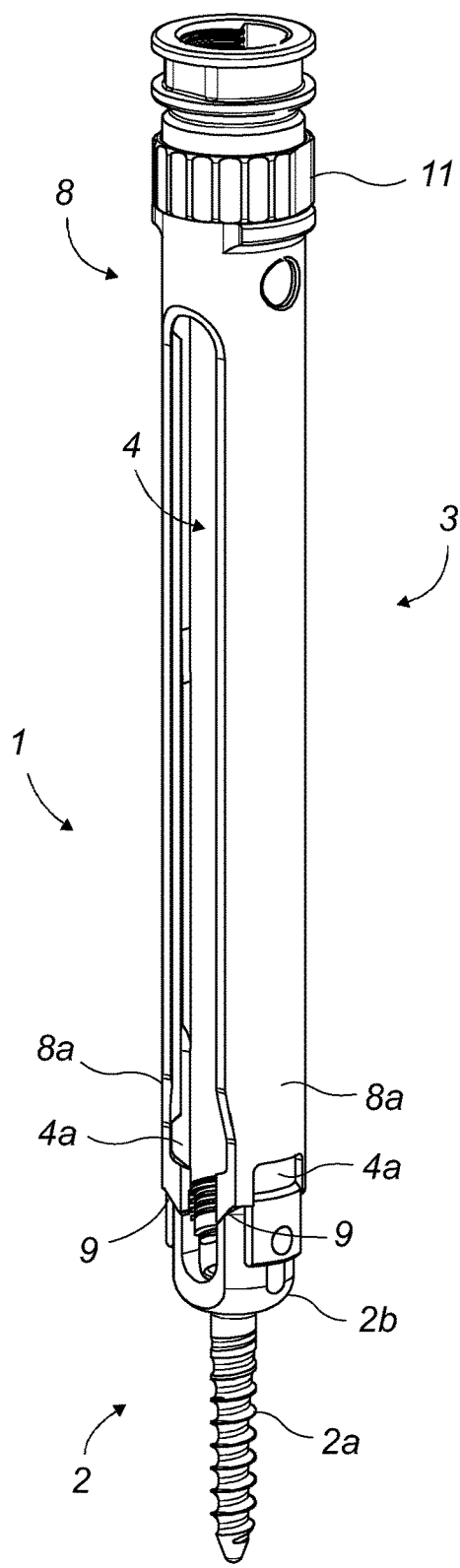
FIG. 13 is a diagrammatic perspective view similar to the FIG. 10 view, showing the locking of the locking position of the outer tube of the extension device.

Said locking member may be in form of a clamping nut (11) suitable for cooperating with a threaded outside portion (10) of the end of the inner tube (4) that is opposite from the branches (4a). With reference to FIG. 13, said threaded outside portion (10) receives the clamping nut (11) that can be tightened until it comes into abutment against the outer tube (8) and comes to prevent said outer tube (8) from sliding into its non-locking position. The clamping nut (11) holds the outer tube (8) in its locking position.

Figure 14:
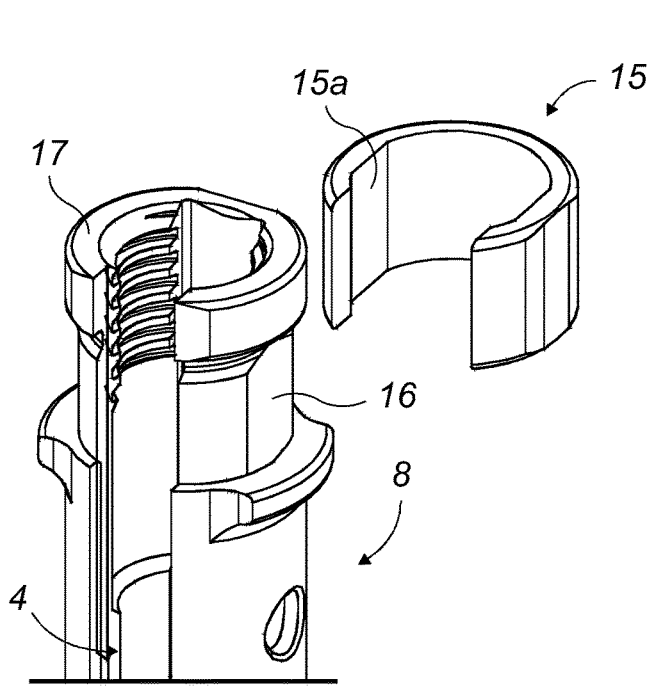
FIG. 14 is a diagrammatic perspective view showing the end of the extension device about to receive a locking member in the form of an open ring.
Figure 15:
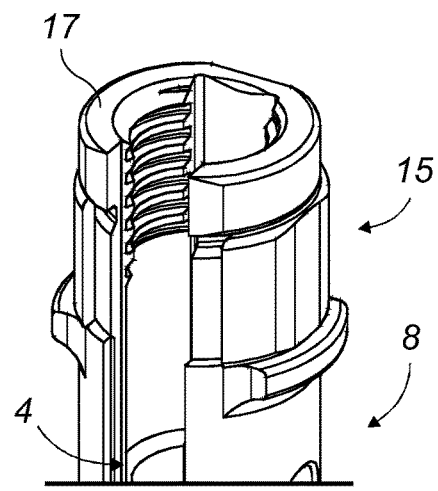
FIG. 15 is a diagrammatic view similar to the FIG. 14 view, the ring being snap-fastened to the end of the extension device.
Figure 16:
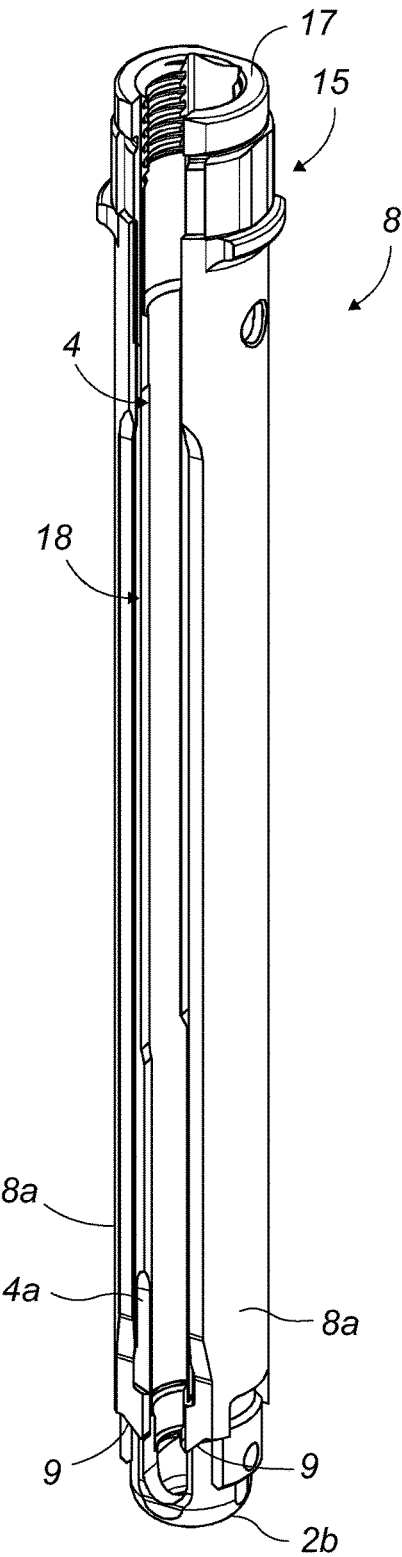
FIG. 16 is a diagrammatic view showing the device of the invention having a longitudinal opening provided all the way along said device.

This locking member may, for example, with reference to FIGS. 14, 15, and 16, be in the form of an open ring (15) that can be inserted transversely onto the end of the inner tube (4) that is opposite from the branches (4a). The ring (15) is inserted between firstly a shoulder (17) provided at the end of the inner tube (4) and secondly the end of the outer tube (8). The ring (15) can be inserted only when the outer tube (8) is in the locking position. The open ring (15) has resilience enabling it to come and snap-fasten around the inner tube (4). Its resilience enables it to remain in place once snap-fastened. The open ring (15) advantageously and internally has straight faces or "flats" (15a) co-operating with complementary flats (16) provided on the outside surface of the inner tube (4) in a manner such as to prevent said open ring (15) from turning once it is snap-fastened.

Once inserted, the ring (15) prevents the outer tube (8) from returning to its non-locking position. The opening in the ring (15) coincides with the space available between the two branches (8a) of the outer tubes (8) and between the two branches (4a) of the inner tube (4), sand thus makes it possible to provide a longitudinal opening (18) all the way along the extension device (3). This longitudinal opening (18) makes it possible to facilitate insertion of a link rod.

The inner tube (4) and the outer tube (8) are also provided with complementary guide means suitable for preventing said outer tube (8) from turning relative to said inner tube (4). These means may be of any suitable type, such as, for example, in the form of a longitudinal rib (not shown) provided on the outside surface of the inner tube (4) and in the form of a corresponding slot (not shown) receiving the rib and provided in the thickness of the outer tube (8).

Figures 11, 12:
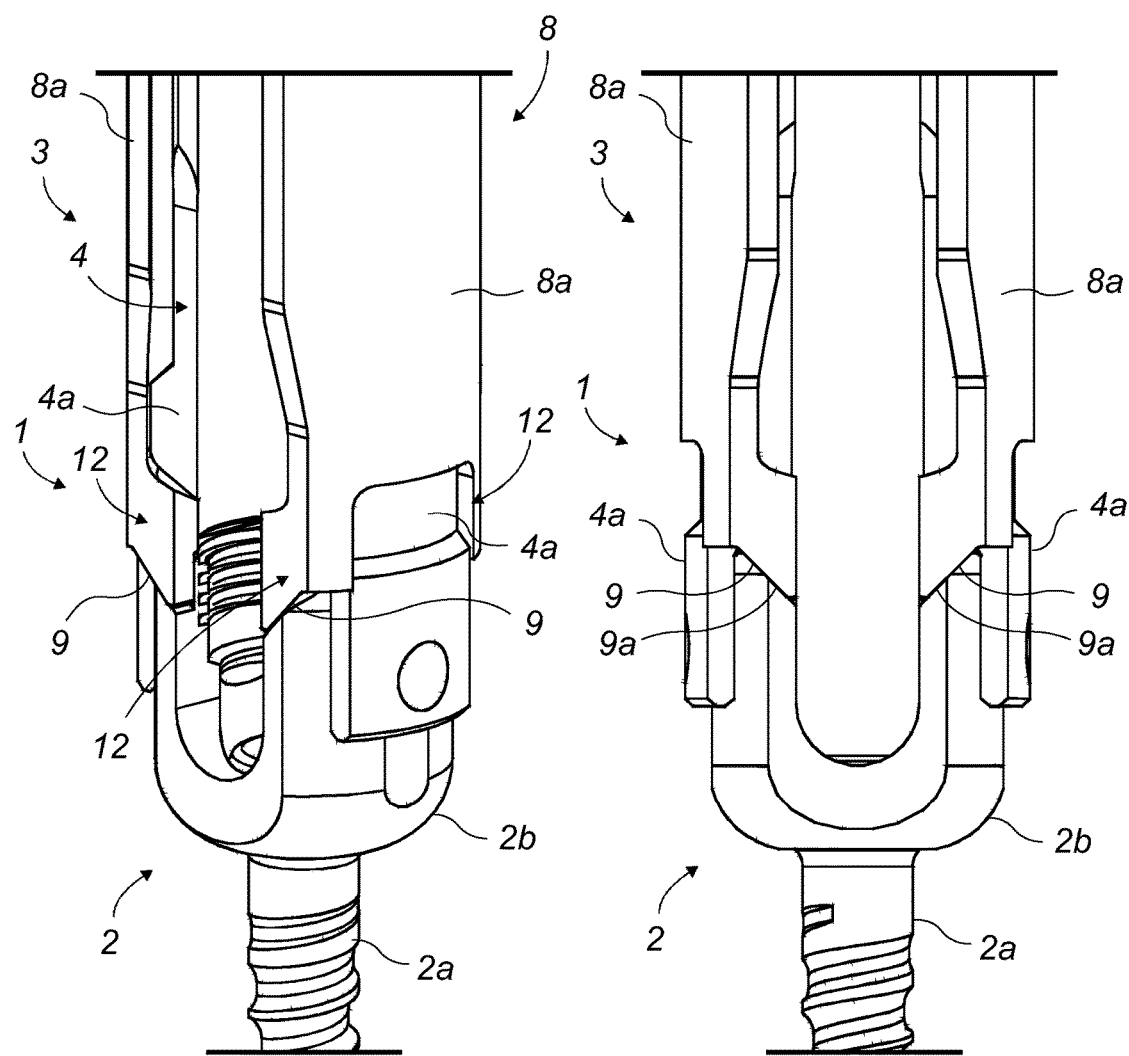
FIG. 11 is a diagrammatic perspective view similar to the FIG. 10 view, showing in detail the co-operation between the outer tube in its locking position and the pedicle screw.
FIG. 12 is a diagrammatic view similar to the FIG. 11 view, showing the assembly as seen from the front.

With reference to FIG. 11, the guiding may, for example, be performed at the ends of the branches (8a) of the outer tube (8), which branches (8a) may be subdivided into two fingers (12) arranged on either side of the branch (4a) of the inner tube (4), the two fingers (12) being guided relative to said branch (4a) of the inner tube (4). In a particular embodiment, it is the two fingers (12) of each branch (8a) of the outer tube (8) that have the contact surfaces (9) suitable for locking the snap-fastening of said branches (8a).

The branches (4a) of the inner tube (4) have resilience enabling them to move apart from each other or to move towards each other. In order to come to fit over a socket (2b), the branches (4a) of the inner tube (4) must be moved apart from each other. The moving apart may be performed automatically by co-operation between the socket (2b) and the branches (4a), in particular via inclined slopes (13), for example (see FIG. 4).

However, when the branches (4a) of the inner tube (4) are provided with lugs (6), or more particularly, when it is necessary to move the branches (4a) of the inner tube (4) apart from each other in order to unlock the extension device (3) from the socket (2b), it can be necessary to use a specific tool (5).

For this purpose, on its inside surface, each of the branches (4a) of the inner tube (4) has a projection or a shoulder (14). Said projections (14) are diametrically opposite each other and in register with each other so that, when an appropriate tool (5) is inserted into the inner tube (4), said tool comes into abutment against said projections (14) so as to force the branches (4a) of the inner tube (4) to move apart from each other (see FIGS. 5 and 6).

With reference to FIG. 2, the specific tool (5) for assisting with putting the extension device (3) in place may be of any suitable type, and may be in the form of a rod (5a) suitable for being inserted into the inner tube (4) of said extension device (3) so as to come into abutment against the projections or shoulders (14) and so as to force the branches (4a) of the inner tube (4) to move apart from each other.

Figure 5:
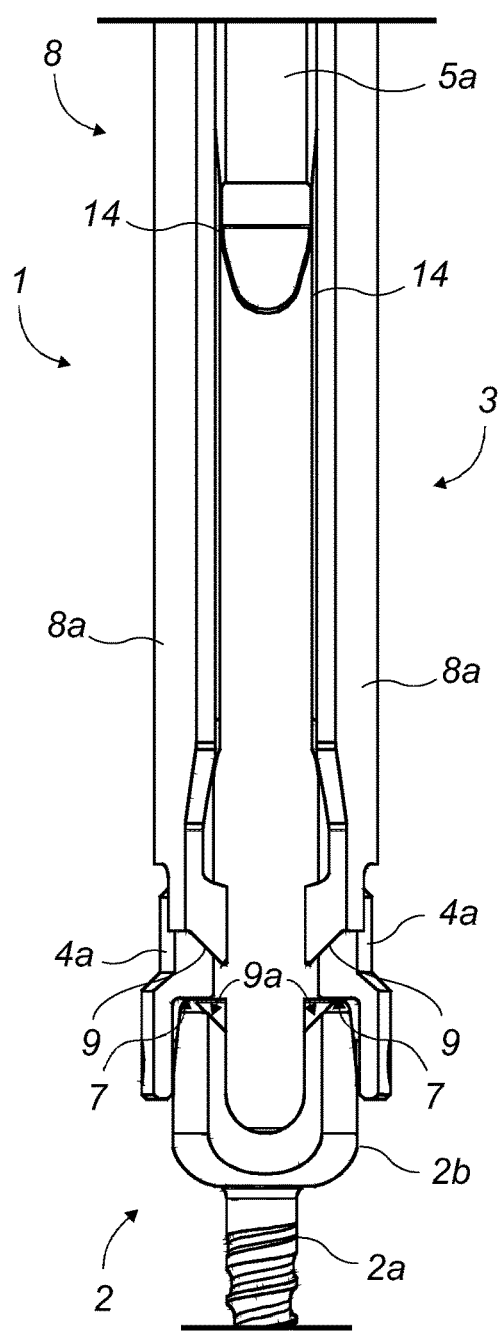
FIG. 5 is a diagrammatic front view showing the extension device as put in place over the socket of a pedicle screw, before the branches of the inner tube are locked onto the outside surface of said socket.
Figure 6:
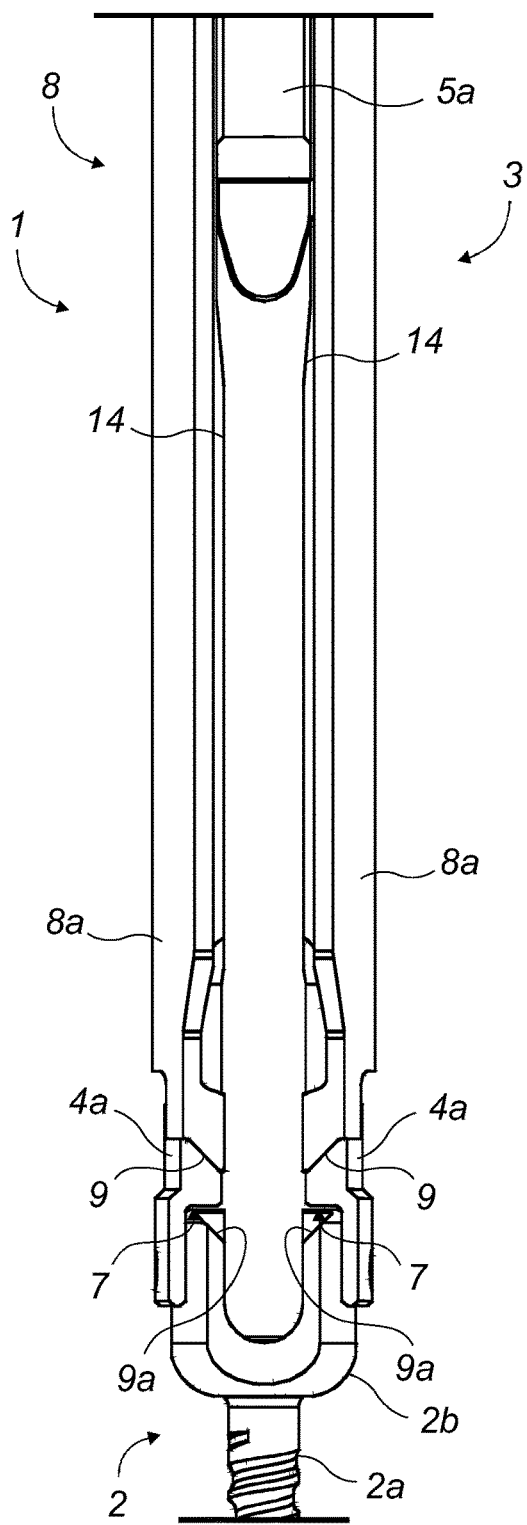
FIG. 6 is a diagrammatic front view similar to the FIG. 5 view, with the tool for assisting with putting in place having been removed and with the branches being locked onto the outside surface of the socket.

Thus, with reference to FIGS. 5 and 6, the tool (5) for assisting with putting the extension device (3) in place may be used equally well either for moving the branches (4a) of the inner tube (4) apart from each other to facilitate putting the extension device (3) into place on the socket (2b), or during unlocking of said extension device (3).

As appears from the above, the invention provides a surgical assembly (1) for treating instabilities, fractures, or deformations of a vertebral column, which assembly comprises an extension device (3) and a pedicle screw (2) that make it possible to preserve access to the socket (2b) of the pedicle screw (2) during the surgical operation, while also optimally holding said extension device (3) temporarily on said screw head (2).

The extension device (3) also makes it possible to facilitate putting a link rod in place for linking pedicle screws (2) together, and to facilitate putting locking members in place for locking said link rod in the socket (2b) of the pedicle screw (2), such link rods and locking members for locking the rods being well known to the person skilled in the art.

The extension device (3) also makes it possible to facilitate putting in place all of the instruments that are necessary for the surgical operation and that enable implants to be put in place and corrections to be made to the vertebral column.

The invention claimed is:

1. A surgical assembly, comprising:
a bone anchorage screw having an anchorage portion for anchoring in a vertebral column, and a head comprising a socket; and
an extension device adapted to fit over the socket of the bone anchorage screw for forming a longitudinal extension thereto;
wherein:
said extension device comprises a first inner tubular element comprising an inside diameter greater than or equal to an inside diameter of the socket of the bone anchorage screw, and extended longitudinally by two diametrically opposite branches, said branches having resilience allowing the branches to be moved apart from each other and towards each other, and free ends of the two branches forming jaws for clamping onto an outside surface of the socket so as to lock onto the socket;

the extension device further comprises a second outer tubular element mounted around the first inner tubular, and element comprising an inside diameter matching an outside diameter of said first inner tubular element to an extent such that said second outer tubular element slides along said first inner tubular element between a non-locking position and a locking position, in which the second outer tubular element does not lock onto and locks onto the bone anchorage screw, respectively, the second outer tubular element being extended longitudinally by two diametrically opposite branches superposed on the branches of the first inner tubular element, free ends of the two branches of the second outer tubular element being in register with the free ends of the two branches of the first inner tubular element, and each of said free ends of the second outer tubular element being provided with first retaining means adapted, when the extension device is fitted over the socket of the bone anchorage screw and when said second outer tubular element is slid into the locking position, for co-operating with complementary second retaining means arranged on the socket to prevent said branches of the second outer tubular element from moving apart from each other, thereby preventing the branches of the first inner tubular element from moving apart from each other so as to maintain the extension device locked onto the socket of the bone anchorage screw; and wherein the first retaining means comprises contact surfaces provided at the ends of the branches of the second outer tubular element that are inclined relative to a transverse plane of the second outer tubular element and face outwards of each branch, and the complementary second retaining means comprises contact surfaces provided on the socket that are inclined relative to a transverse plane of said socket and face towards the inside of the socket, the contact surfaces of the first retaining means and the contact surfaces of the complementary second retaining means being adapted to come to bear against one another when the second outer tubular element is slid into the locking position for preventing the branches of the second outer tubular element from moving apart from each other, wherein contact surface of the first retaining means of each branch of the two diametrically opposite branches are angled away from each other as they extend longitudinally from the ends of the branches.

2. The surgical assembly according to claim 1, wherein complementary fastening means suitable for locking said branches of the first inner tubular element so that they are prevented from moving longitudinally relative to the outside surface of the socket are arranged firstly at the free ends of the branches of the first inner tubular element and on the inside surfaces of said branches that are adapted to be in contact with the outside surface of the socket, and secondly on said outside surface of the socket.

3. An extension device of a surgical assembly, said extension device being adapted to fit over a socket of a bone anchorage screw provided with first retaining means, said extension device comprising:

a first inner tubular element comprising an inside diameter substantially equal to an inside diameter of the socket, and extended longitudinally by two diametrically opposite branches, said branches having resilience allowing them to be moved apart from each other and towards each other, and free ends of the two branches forming jaws adapted for clamping onto an outside surface of the socket so as to lock onto the socket; and a second outer tubular element mounted around the first inner tubular element, and having an inside diameter matching an outside diameter of said first inner tubular element to an extent such that said second outer tubular element slides along said first inner tubular element between a non-locking position and a locking position, in which the second outer tubular element does not lock onto and locks onto the bone anchorage screw, respectively, the second outer tubular element being extended longitudinally by two diametrically opposite branches superposed on the branches of the first inner tubular element, free ends of the two branches of the second outer tubular element being in register with the free ends of the two branches of the first inner tubular element, and each of said free ends of the second outer tubular element being provided with the first retaining means comprising contact surfaces provided at the ends of the branches of the second outer tubular element that are inclined relative to a transverse plane of the second outer tubular element and face outwards of each branch, said contact surfaces are adapted, when said second outer tubular element is slid into the locking position, to come to bear against complementary second retaining means comprising contact surfaces provided on the socket that are inclined relative to a transverse plane of said socket and face towards the inside of the socket, for preventing the branches of the second outer tubular element from moving apart from each other so as to maintain the extension device locked onto the socket of a bone anchorage screw, wherein contact surface of the first retaining means of each branch of the two diametrically opposite branches are angled away from each other as they extend longitudinally from the ends of the branches.

4. The extension device according to claim 3, wherein at least one of the branches of the first inner tubular element has, at its free end, a transverse shoulder suitable for forming an abutment against the socket of the bone anchorage screw when said extension device fits over said socket.

5. The extension device according to claim 3, further comprising a locking member adapted for holding the second outer tubular element in the locking position in which the second outer tubular element onto the bone anchorage screw.

6. The extension device according to claim 3, wherein the first inner tubular element and the second outer tubular element are provided with complementary guide means adapted for preventing the second outer tubular element from turning relative to the first inner tubular element.

7. The extension device according to claim 3, wherein, on its inside surface, each of the branches of the first inner tubular element has a projection diametrically opposite each other and in register with each other so that, when a tool is inserted into the first inner tubular element, said tool comes into abutment against at least one said projection so as to force the branches of the first inner tubular element to move apart from each other.

8. The extension device according to claim 7, further comprising a tool in the form of a rod adapted for being inserted into the first inner tubular element of said extension device so as to come into abutment against the at least one said projection so as to force the branches of the first inner tubular element to move apart from each other.

9. The surgical assembly according to claim 1, wherein pairs of the contact surfaces of the complementary second retaining means of the socket are diametrically opposite each other across a respective opening in the socket, and wherein the pairs of the contact surfaces of the complementary second retaining means of the socket are angled away toward each other as they extend longitudinally towards the anchorage portion of the bone anchorage screw.

10. The surgical assembly according to claim 1, wherein pairs of the contact surfaces of the complementary second retaining means of the socket are diametrically opposite each other across a respective opening of a pair of diametrically opposite openings in the socket, and wherein the pairs of the contact surfaces of each of the two diametrically opposite branches of the outer tubular element are positioned within a respective opening of the pair of diametrically opposite openings in the socket when the second outer tubular element is positioned in the locking position.

* * * * *